(12) United States Patent
Yoshida et al.

(10) Patent No.: US 6,649,154 B1
(45) Date of Patent: Nov. 18, 2003

(54) HAIRDRESSING COSMETIC PREPARATION AND HAIRDRESSING METHOD USING THE SAME

(75) Inventors: Katsunori Yoshida, Yokohama (JP); Daigo Mizumoto, Yokohama (JP); Tomoyuki Kawasoe, Yokohama (JP); Yoshiharu Tsuji, Yokohama (JP); Toshio Yanaki, Yokohama (JP); Masaaki Uemura, Yokohama (JP); Kaoru Ichikawa, Tokyo (JP); Hideko Saito, Tokyo (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/584,338

(22) Filed: Jun. 1, 2000

(30) Foreign Application Priority Data

| | | |
|---|---|---|
| Jun. 3, 1999 | (JP) | 11-156792 |
| Mar. 30, 2000 | (JP) | 2000-095024 |

(51) Int. Cl.$^7$ .............................. A61K 7/06; A61K 7/00
(52) U.S. Cl. ................... 424/70.13; 424/401; 424/70.1; 424/70.11
(58) Field of Search ............... 424/401, 70.1, 424/70.11, 70.13

(56) References Cited

U.S. PATENT DOCUMENTS 5,158,772 A * 10/1992 Davis
6,197,318 B1 * 3/2001 Abe et al.
6,197,319 B1 * 3/2001 Wang et al.

FOREIGN PATENT DOCUMENTS

| | | |
|---|---|---|
| EP | 0 409 488 | 1/1991 |
| EP | 0 469 232 A1 | 2/1992 |
| JP | 8225435 | 9/1996 |
| JP | 08-225435 | 9/1996 |
| JP | 08-231354 | 9/1996 |
| JP | 08231354 | 9/1996 |
| JP | 09-030936 | 2/1997 |
| JP | 09278634 | 10/1997 |
| JP | 09-278634 | 10/1997 |

OTHER PUBLICATIONS

Pureglucan, Takeda Vitamin and Food, 1997.*

* cited by examiner

Primary Examiner—Thurman K. Page
Assistant Examiner—Rachel M. Bennett
(74) Attorney, Agent, or Firm—Venable LLP; Fei-Fei Chao

(57) ABSTRACT

The hairdressing cosmetic preparation of the present invention is characterized by comprising a heat-gelling polymer which becomes to gel upon heating. The gelling temperature of the heat-gelling polymer is preferably 60° C. or higher. Preferable heat-gelling polymer is polysaccharides such as β-1,3-glucan, β-1,3-xylan, curdlan and the like. The hair dressing preparation of the present invention, due to using such heat-gelling polymer, can give excellent hairdressing effect and hair-setting power when hair applied with the hairdressing preparation is treated with heating.

18 Claims, No Drawings

HAIRDRESSING COSMETIC PREPARATION AND HAIRDRESSING METHOD USING THE SAME

RELATED APPLICATIONS

This application claims the priority of Japanese Patent Application No. 11-156792 filed on Jun. 3, 1999 and Japanese Patent Application No.2000-95024 filed on Mar. 30, 2000, which are incorporated herein by reference.

FIELD OF THE INVENTION

The present invention relates to a hairdressing cosmetic preparation and a hairdressing method using the same; and, in particular, to an improvement in a setting agent thereof.

BACKGROUND OF THE INVENTION

Among hair cosmetic preparations conventionally in wide use, hairdressing cosmetic preparation for hairdressing and set-keeping include those in which a hairdressing oil component such as polypropylene oxide monobutyl ether, polypropylene oxide glyceryl ether, or their phosphate ester or salt is dissolved in or emulsified with water, a lower alcohol, their mixed solvent, or the like; those in which a high-molecular compound having a coat-forming property and a setting property is dissolved in water, a lower alcohol, their mixed solvent, or the like; and so forth.

Although the hair applied with the former hairdressing cosmetic preparations compounded with the hairdressing oil component is free of stiffness, there have been problems that the hair glares is so sticky that its touch is not so favorable.

On the other hand, although the latter hairdressing cosmetic preparations compounded with the high-molecular compound are excellent in their action of securing hairs to each other and keeping their setting, there have been problems that the hair applied with the hairdressing cosmetic preparations has stickiness and is not smooth in the process of applying, drying and finishing, and become severely stiff after drying.

When a large amount of a polymer as a setting agent is compounded into the preparation in order to enhance its hair setting effect, in particular, combing has become more difficult upon blowing by use of a drier or the like, and stiffness in hair or separation (flaking) of the setting agent has occurred after the drying.

For overcoming such problems, improvements have been proposed by compounding various additives such as polyhydric alcohols, their derivatives, lanolin, and esters. However, the setting effect may deteriorate along with their addition, so that there have been cases where satisfactory hairdressing preparations are not obtained. Similarly, although the touch of hair improves when the amount of the polymer used as a setting agent is lowered, hairdressing preparations satisfactory in terms of the setting effect have not been obtained.

SUMMARY OF THE INVENTION

The present invention is performed in view of the above-mentioned problems of the prior art, and it is an object of the present invention to provide a hairdressing cosmetic preparation having a favorable touch and an excellent setting effect.

The inventors have carried out diligent studies in order to achieve the above-mentioned object and, as a result, have found that a favorable touch and a high setting effect can be obtained if a polymer which becomes to gel upon heating is compounded as a hairdressing effective component into a hairdressing cosmetic preparation and heated with a dryer or the like when applied to hair, thereby accomplishing the present invention.

Namely, a hairdressing cosmetic preparation in accordance with the present invention is characterized by comprising a heat-gelling polymer which becomes to gel upon heating.

In the hairdressing cosmetic preparation, it is preferable that the heat-gelling polymer has a gelling temperature of 60° C. or higher.

Also, in the hairdressing cosmetic preparation, the heat-gelling polymer is preferably a polysaccharide.

Also, in the hairdressing cosmetic preparation, the heat-gelling polymer is preferably β-1,3-glucan.

Also, in the hairdressing cosmetic preparation, the heat-gelling polymer is preferably β-1,3-xylan.

Also, in the hairdressing cosmetic preparation, the heat-gelling polymer is preferably curdlan.

Also, in the hairdressing cosmetic preparation, it is preferable that the heat-gelling polymer which is powder in an ungelled state and/or in a dissolved neutralized gel state is dispersed into the cosmetic preparation.

Also, in the hairdressing cosmetic preparation, it is preferable that water is further contained therein.

Also, in the hairdressing cosmetic preparation, it is preferable that the heat-gelling polymer is 0.001% to 10% by weight in the cosmetic preparation.

Also, in the hairdressing cosmetic preparation, it is preferable that a fine particle powder is contained therein.

Also, in the hairdressing cosmetic preparation, the fine particle powder is preferably fine particle titanium dioxide.

Also, in the hairdressing cosmetic preparation, the fine particle powder is preferably fine particle silica.

Also, in the hairdressing cosmetic preparation, the fine particle powder is preferably silica-surface-treated fine particle titanium dioxide.

A hairdressing method in accordance with the present invention is characterized by comprising the steps of shaping hair while applying thereto a composition comprising a heat-gelling polymer, and then fixating the hair with a hot wind.

In the method, it is preferable that water exists upon application to the hair and the hot wind is 80° C. or higher.

BEST MODES FOR CARRYING OUT THE INVENTION

The hairdressing cosmetic preparation of the present invention includes a heat-gelling polymer which becomes to gel upon heating. After the hairdressing cosmetic preparation of the present invention is applied to hair, the aimed hair style is fixated with a heat from a drier or the like.

The heat-gelling polymer used in the present invention gels at a heating temperature of 60° C. or higher. Examples thereof include heat-coagulable proteins, collagen, heat-coagulable starches, and the like. The molecular weight is, but not limited thereto, within the range from 10,000 to 10,000,000 normally. Among them, preferable are heat-gelling polysaccharides, and more preferable is β-1,3-glucan or β-1,3-xylan.

Further, in β-1,3-glucan, straight-chain type curdlan is the most preferable from the viewpoint of its stability in supply and its cost. When β-1,3-glucan other than curdlan, for example, such as scleroglucan, sclerotan, schizophyllan, lentinan, paramylon, callose, laminaran, or the like is processed by such a method as mild Smith decomposition (Polym J. 13(12) 1135–1143 (1981)), a polymer having properties similar to those of curdlan can be obtained.

More specifically, curdlan is a kind of polysaccharides produced by a microorganism (Alcaligenes faecalis var. myxogenes, various strains of Agrobacterium, or Rhizobium). Its constituent sugar is D-glucose alone, and 99% of its glucoside bonds is β-1,3-bond.

Known as a method for preparing a dispersion is one comprising the steps of adding water to curdlan powder and vigorously stirring the mixture by use of a high-speed homogenizer, cutter mixer, or the like or the steps of adding curdlan to warm water of about 55° C. while stirring it with a hand, a propeller stirrer, or the like and then cooling the mixture, thereby yielding a uniform dispersion of ungelled powder. A gel is formed when this aqueous dispersion is heated.

Also, without heating, a gel can be formed if curdlan is once dissolved in an alkaline aqueous solution of sodium hydroxide or the like and then is neutralized by addition of a neutralizing equivalent amount of an acid such as hydrochloric acid. In this specification, such a gel is referred to as dissolved neutralized gel. A stable dispersion can be obtained if this dissolved neutralized gel is vigorously stirred by a homogenizer or the like so as to be finely crushed. A gel is formed when this dispersion is heated. Here, a gel, that has a similar nature with the dissolved neutralized gel, can also be made when curdlan dissolved in the alkaline aqueous solution is neutralized with carbonic acid gas or the like while standing still, or when the alkali such as sodium hydroxide is eliminated by use of a dialysis membrane. A gel, that has a similar nature with the dissolved neutralized gel, can also be made when the hydroxyl group dissociated upon addition of a cation such as calcium or magnesium ion to the alkaline aqueous solution forms a cross-linked structure with the cation.

Gels obtained upon heating can be roughly divided into two types according to their processing temperature. Namely, they are thermally irreversible gels obtained by heating at 80° C. or higher and thermally reversible gels obtained by cooling after heating at about 60° C., which can be called as high-set gels and low-set gels, respectively. Hairdressing cosmetic preparations containing the high-set gels tend to exhibit a slightly lower hairdressing power. The low-set gels are sufficiently usable although their effects are inferior to those of ungelled powder or dissolved neutralized gel.

In a particularly preferred example of the present invention, a hairdressing cosmetic preparation including an ungelled powder or dissolved neutralized gel of curdlan is applied on hair and is heated and dried with a hot wind at a low-set gelling temperature (60° C.) or higher, more preferably at a high-set gelling temperature (80° C.) or higher, whereby excellent hairdressing power and set-keeping power can be obtained.

Polymers gelling at a temperature less than 60° C. are unfavorable not only in that they may gel in containers when placed under severe conditions to be disadvantageous in their use, but also in that their effects may not fully be exhibited when applied on hair.

In the present invention, one or more kinds of the above-mentioned heat-gelling polymers may be used. The amount thereof is 0.001% to 10% by weight, preferably 0.01% to 1% by weight, with respect to the total amount of the hairdressing cosmetic preparation. The hairdressing power and hairdressing-keeping power may be insufficient if the amount is less than 0.001% by weight, whereas unfavorable stiffness and flaking may occur if the amount exceeds 10% by weight.

Also, the hairdressing cosmetic preparation of the present invention achieves a light finish, and does not exhibit stiffness, coarseness, or oiliness even after drying, thereby giving a very favorable touch to the hair as if nothing is applied thereon. On the other hand, its feel of use is so light upon styling that hair may not be caught by combs, brushes, and fingers very well. For improving the feel of use of the hairdressing cosmetic preparation in accordance with the present invention upon styling without deteriorating its favorable feel of finish, compounding a fine particle powder therein is effective. If the fine particle powder is contained therein, hair will appropriately be caught by combs and the like upon styling, so that operations such as straightening unruly hair, straight blow, shaping blow, and the like become much easier, thus remarkably improving usability.

The fine particle powder preferably has an average particle size of 0.001 to 0.15 $\mu$m from the viewpoint of easiness in styling, feel of finish, and the like. A powder having a pigment class particle size of 0.2 $\mu$m or greater may be inferior in the touch after finishing although the usability upon styling can be improved thereby.

As the fine particle powder, any of inorganic and organic powders can be used, and two or more kinds thereof can also be used in combination. Examples of inorganic powder include talc, mica, kaolin, sericite, silica, titanium oxide, magnesium carbonate, calcium carbonate, aluminum silicate, barium silicate, calcium silicate, magnesium silicate, metal tungstate, magnesium, zeolite, barium sulfate, calcined calcium sulfate, calcined plaster, calcium phosphate, fluorine apatite, hydroxy apatite, ceramic powder, metallic soap, zinc oxide, and the like. Examples of organic powder include nylon powder, polyethylene powder, cellulose powder, polymethyl methacrylate (PMMA) powder, polyamide resin powder, polystyrene powder, and the like. These fine particle powders may be subjected to known surface treatments with metallic soap, silicone, cation, dextrin, fatty acids, alumina, silica, fluorides, and the like.

The amount of the fine particle powder is 0.01% to 5% by weight, preferably 0.05% to 2% by weight in the hairdressing cosmetic preparation. The usability upon styling may not improve if the amount is too small, whereas the feel of finish may deteriorate if the amount is too large.

The fine particle powder of the present invention is preferably fine particle titanium dioxide or fine particle silica or their surface-treated powder. Particularly preferred is fine particle titanium dioxide having been surface-treated with silica. Since the surface electric charge of the silica-surface-treated fine particle titanium dioxide is adjusted by silica, they can stably disperse on a primary particle level in a neutral region, thus yielding a very high transparency. Such silica-surface-treated fine particle titanium dioxide is also known as super fine particle titanium dioxide, and is usually used as its aqueous dispersion (titania sol) for compounding.

Without being restricted in particular, the hairdressing cosmetic preparation of the present invention can be any form, and can be manufactured by a common method while further containing various kinds of ingredients which are usually compounded into hairdressing cosmetic preparations within a range not deteriorating the effect of the present invention in addition to the above-mentioned essential ingredients. For example, hairdressing cosmetic preparations such as hair cream, hair lotion, a foamy hairdressing preparation like a hair foam, hair gel, hair mist (non-gas type), hair spray, hair liquid, and hair wax can be provided.

Examples of known ingredients commonly used in hairdressing cosmetic preparations such as hairdyes and hairdressing preparations include, as alcohol, not only aliphatic alcohols which are hard to dissolve in water, such as n-butyl alcohol, sec-butyl alcohol, cyclohexanol, butyl cellosolve, benzyl alcohol, 2-phenoxy ethanol, and phenyl ethanol, but also aromatic alcohols, polyhydric alcohols, and the like.

Examples of pH adjusters include organic acids such as citric acid, malic acid, acetic acid, lactic acid, oxalic acid, tartaric acid, formic acid, and levulinic acid, and inorganic acids such as phosphoric acid and hydrochloric acid.

Further examples of additives include humectants such as glycerin, propylene glycol, dipropylene glycol, polyethylene glycol, chondroitin sulfate, hyaluronic acid salts, diglycerin, 1,3-butylene glycol, sorbitol, maltitol, pyrrolidone carboxylate, lactose, and olygosaecharides; oily ingredients such as lanolin, squalane, liquid paraffin, vaseline, higher fatty acids, triglyceride, and ester oils; and silicones such as methylphenyl polysiloxane, dimethyl siloxane/methyl (polyoxyethylene) siloxane copolymer, rubber-like dimethyl polysiloxane, and amino-modified polysiloxane.

Also, protein hydrolysates such as collagen hydrolysate, keratin hydrolysate, silk protein hydrolysate, elastin hydrolysate, and bean protein hydrolysate and their quaternary salts can be compounded.

As an emulsifier, other amphipatic materials and surfactants can also be used.

Examples of nonionic surfactants include polyoxyethylene type surfactants such as polyoxyethylene alkyl ethers, polyoxyethylene fatty acid esters, polyoxyethylene polyhydric alcohol fatty acid partial esters, and polyoxyethylene hardened castor oil derivatives; alkyl polyglycosides such as octylpolyglycoside; polyglycerin type surfactants such as polyglycerin fatty acid esters and polyglycerin alkyl ethers; sugar alcohol ethers such as maltitol hydroxyalkyl ethers; and fatty acid diethanol amides.

Examples of anionic surfactants include higher fatty acid salts, alkyl benzene sulfonic acid salts, phosphoric acid esters, alkyl sulfuric acid salts, alkyl sulfuric acid ester salts, polyoxyethylene alkyl sulfuric acid ester salts, and the like. Also, cationic surfactants such as amino acids, alkyl trimethyl ammonium salts, dialkyl dimethyl ammonium salts, and alkyl dimethylamine oxide, and other surfactants can be used as appropriate.

Further, for example, lower alcohols such as butanol, propanol, and isopropanol; higher alcohols such as 2-ethylhexyl alcohol, 2-hexyldecyl alcohol, 2-decyltetradecyl alcohol, isostearyl alcohol, cetostearyl alcohol, lauryl alcohol, oleyl alcohol, myristyl alcohol, palmityl alcohol, stearyl alcohol, and cetyl alcohol; and the like can be compounded.

Examples of sequestering agents and antiseptics include hydroxyethane disulfonic acid salts, phenacetin, EDTA and its salts, parabens, and stannic acid salts. Examples of high-molecular compounds include poly(dimethylallyl ammonium halide) type cationic polymers; cationic polymers of a condensate type of tauroylamine obtained from polyethylene glycol, epichlorohydrin, propyleneamine, and tallow fatty acid; cationic polymers of a condensate type of cocoylamine obtained from polyethylene glycol, epichlorohydrin, propyleneamine, and coconut fatty acid; cationic polymers of a vinyl pyrrolidone/dimethylamino methacrylate copolymer type; and cationic polymers of cellulose ether type containing quaternary nitrogen.

Also, thickeners such as carboxy methyl cellulose, carboxy vinyl polymer, hydroxy ethyl cellulose, hydroxy propyl cellulose, methyl cellulose, xanthan gum, carrageenan, alginic acid salts, pectin, furcellaran, gum arabic, ghatti gum, karaya gum, tragacanth gum, agar powder, bentonite, cross-linking polyacrylic acid salts, and the like can also be used within a range where the effect of the present invention is not deteriorated.

As resins, nonion resins such as polyvinyl pyrrolidone, vinyl pyrrolidone/vinyl acetate copolymer, and polyvinyl alcohol; anion resins such as acrylic resin alkanol amine solutions, acrylic acid ester/methacrylic acid ester copolymer, acrylic acid ester/acrylamide/acrylic acid copolymer, vinyl methyl ether/butyl malate copolymer, and chloric o-[2-hydroxy-3-(trimethylammonio) propyl] hydroxy ethyl cellulose; cationic resins such as vinyl pyrrolidone/dimethyl amino ethyl methacrylate cationized copolymer; and amphoteric resins such as hydroxypropyl acrylate/butylaminoethyl methacrylate/acrylic acid octylamide copolymer and N-methacryloyl oxyethyl N,N-dimethyl ammonium-α-N-methyl carboxy betaine/alkyl methacrylate copolymer can also be compounded. In the above, acrylic resin alkanol amine solutions, vinyl pyrrolidone/dimethyl amino ethyl methacrylate cationized copolymer and N-methacryloyl oxyethyl N,N-dimethyl ammonium-α-N-methyl carboxy betaine/alkyl methacrylate copolymer are preferable. If resins are compounded, then the usability upon styling can be improved to a certain extent. While hair continuously has favorable tension from the start of blowing to the end thereof in the case of fine particle powder, tension is felt when hair is dried to a certain extent in the case of resins.

In addition, perfumes, medicaments, and the like can selectively be used as required.

Also, not only organic and inorganic pigments but also lakes may be compounded in the hairdressing cosmetic preparation of the present invention within a range where the effect of the present invention is not deteriorated.

Examples of organic pigments include azo type pigments, indigo type pigments, and phthalocyanine type pigments. Examples of inorganic pigments include red oxide of iron, yellow oxide of iron, black oxide of iron, chromium oxide, ultramarine, iron blue, carbon black, and the like. Examples of lakes include not only lake pigments such as Red Nos. 202, 204, 206, 207, and 220, but also dye lakes such as aluminum lake.

In the case where the hairdressing cosmetic preparation of the present invention is formed into hair spray, liquefied petroleum gas (L.P.G.) mainly composed of propane, butane, and isobutane; a pressurized gas such as dimethyl ether, carbonate gas, or nitrogen gas; and the like can be used alone or in their mixture as a propellant. Among them, liquefied petroleum gas (L.P.G.) is preferred in particular. The ratio between the stock solution of the hairdressing cosmetic preparation in accordance with the present invention and the propellant is preferably such that the propellant is 95 to 5 parts by weight with respect to 5 to 95 parts by weight of the stock solution.

EXAMPLES

In the following, the present invention will be explained more specifically with reference to Examples, which do not restrict the present invention. The compounding amount will be expressed by % by weight unless otherwise specified.

I. Kinds of Polymers and Hairdressing Power (Test Examples 1 to 10)

As the heat-gelling polymers, those shown in Table 1 were used for preparing hairdressing cosmetic preparations. The polymers used in Test Examples 5 to 9 were those in which side chains were thinned out by mild Smith decomposition. In Test Example 10, xanthan gum which could not gel upon heating, was used as a comparative example. Purified water and sodium hydroxide were added to each polymer to be uniformly dissolved, and then the mixture was neutralized with hydrochloric acid. Further, the rest ingredients were added and dissolved into ethanol. The resulting solution was mixed with the neutralized solution mentioned above to prepare a hairdressing cosmetic preparation.

| | |
|---|---|
| Polymer (Table 1) | 0.2 wt % |
| Sodium hydroxide (1 mol/L) | 1.0 |
| Hydrochloric acid (1 mol/L) | 1.0 |
| 1-Menthol | 0.2 |
| Ethanol | 40.0 |
| Perfume | Q.S. |
| Purified water | Balance |

Hair after hairdressing was evaluated according to the following method. Comparative evaluations were made according to Half-Head method (half-head comparing method) by 20 male panels. Namely, after the hair was washed with a commercially available shampoo and then completely dried, 10 g of the hairdressing cosmetic preparation in accordance with the present invention were applied to the half of the hair, whereas 10 g of the comparative preparation (Test Example 10) were applied to the other half, and hairdressing was carried out while being blown with a hot wind at 80° C. or higher. Then, sensory evaluations were carried out.

The evaluations were effected with respect to four items of "hairdressing power," "gloss," "suppleness," and "stickiness." The sensory evaluations were performed by one-to-one comparison of the hairdressing cosmetic preparation of the present invention with reference to the comparative preparation according to the following five-step evaluations, and their results are shown in Table 2 as average evaluation points of 20 male panels.

Evaluation Points:

+2: superior to the comparative preparation

+1: slightly superior to the comparative preparation

0: on a parallel with the comparative preparation

−1: slightly inferior to the comparative preparation

−2: inferior to the comparative preparation

TABLE 1

| Test Example No. | Polymer |
|---|---|
| 1 | Curdlan |
| 2 | Heat-coagulable starch |
| 3 | Heat-coagulable collagen |
| 4 | β-1,3-xylan |
| 5 | Paramylon |
| 6 | Scleroglucan |
| 7 | Laminaran |
| 8 | Schizophyllan |
| 9 | Lentinan |
| 10 | Xantan gum |

TABLE 2

| Test Example No. | Hairdressing power | Gloss | Suppleness | Stickiness |
|---|---|---|---|---|
| 1 | 1.8 | 1.5 | 1.7 | 1.6 |
| 2 | 1.5 | 1.4 | 1.6 | 1.3 |
| 3 | 1.5 | 1.4 | 1.5 | 1.7 |
| 4 | 1.7 | 1.4 | 1.4 | 1.6 |
| 5 | 1.5 | 1.2 | 1.4 | 1.5 |
| 6 | 1.3 | 1.5 | 1.5 | 1.3 |
| 7 | 1.4 | 1.6 | 1.4 | 1.5 |
| 8 | 1.7 | 1.5 | 1.4 | 1.5 |
| 9 | 1.6 | 1.6 | 1.3 | 1.6 |

As can be seen from Table 2, those using the heat-gelling polymers of Test Examples 1 to 9 exhibited vary excellent results in each item of hairdressing power, gloss, suppleness, and stickiness as compared with Test Example 10 in which xanthan gum having no heat-gelling property was used.

II. Kinds of Polymers and Set-Keeping Power (Test Examples 11 to 21)

As the heat-gelling polymers, those shown in Table 3 were used to prepare emulsified compositions of the following formulations, and their set-keeping power, lack of stickiness, and lack of stiffness were evaluated. Their results are shown in Table 4. The method of evaluations will be explained later. The polymers used in Test Examples 15 to 19 were those in which side chains were thinned out by mild Smith decomposition. Test Examples 20 and 21 were comparative examples using polymers which would not gel upon heating.

(Emulsified Composition Formulation)

| | |
|---|---|
| Phase A: | |
| Polymer (Table 3) | 0.5 wt % |
| Sodium hydroxide (1 mol/L) | 1.0 |
| Hydrochloric acid (1 mol/L) | 1.0 |
| Ion-exchanged water | 50.0 |
| Phase B: | |
| Ethanol | 5.0 |
| Perfume | Q.S. |
| Phase C: | |
| POE hardened castor oil | 0.5 |
| Propylene glycol | 2.0 |
| Methyl polysiloxane | 1.0 |
| Ion-exchanged water | Balance |

(Method of Preparing Emulsified Composition)

After ion-exchanged water and aqueous sodium hydroxide solution were added to the polymer and uniformly dissolved, the mixture was neutralized with hydrochloric acid, whereby phase A was obtained. Ethanol and perfume were mixed to obtain phase B. The ingredients of phase C were emulsified with a homomixer. Phases B and C were added to phase A, thereby obtaining the emulsified composition.

(Evaluating Method)

(1) Set-Keeping Power

A strand of hair having a length of 25 cm and a weight of 2 g was wetted with water and, with 0.5 g of the sample applied thereto, was wound about a rod having a diameter of 15 mm, which was then dried for 30 minutes within a thermostat bath at 80° C. After the drying, the rod was removed from the curled strand. The strand was hung in a thermo-hygrostat box (28° C., 90% RH) for 1 hour, and then the length of curl was measured. The set-keeping power was calculated from the length of curl immediately after being removed from the rod (L1 cm) and the length thereof after being hanging for 1 hour (L2 cm) according to the following equation:

Set-keeping power=$\{(25-L2)/(25-L1)\} \times 100$

Indication of Measurement Results:
⊚: set-keeping power of 90% to 100%
○: set-keeping power of 67% to 89%
Δ: set-keeping power of 34% to 66%
X: set-keeping power of 0% to 33%

(2) Lack of Stickiness from Application to Drying

A strand of hair (4 g) coated with 2 g of the sample was shaped with a comb, and its stickiness before drying was subjected to a sensory evaluation.
○: no stickiness at all
Δ: slight stickiness
X: considerable stickiness (3) Lack of Stiffness in Finished Hair A strand of hair (4 g) coated with 2 g of the sample was shaped with a comb, dried, and then subjected to a sensory evaluation according to the following standards:
○: no stiffness at all
Δ: slight stiffness
X: considerable stiffness

TABLE 3

| Test Example No. | Polymer |
|---|---|
| 11 | Curdlan |
| 12 | Heat-coaguable starch |
| 13 | Heat-coagulable collagen |
| 14 | α-1,3-xylan |
| 15 | Paramylon |
| 16 | Scleroglucan |
| 17 | Laminaran |
| 18 | Schizophyllan |
| 19 | Lentinan |
| 20 | Carboxy methyl cellulose |
| 21 | Polyvinyl pyrrolidone/vinyl acetate copolymer |

TABLE 4

| Test Example No. | Evaluation Items | | |
|---|---|---|---|
| | Set-keeping power | Stickiness | Stiffness |
| 11 | ⊚ | ○ | ○ |
| 12 | ○ | ○ | ○ |
| 13 | ○ | ○ | ○ |
| 14 | ○ | ○ | ○ |
| 15 | ○ | ○ | ○ |
| 16 | ⊚ | ○ | ○ |
| 17 | ○ | ○ | ○ |
| 18 | ○ | ○ | ○ |
| 19 | ⊚ | ○ | ○ |
| 20 | X | Δ | X |
| 21 | X | X | X |

As can be seen from the results of Table 4, the hairdressing cosmetic preparations containing the heat-gelling polymers shown in Test Examples 11 to 19 were excellent in set-keeping power and exhibited a favorable touch.

III. Compounding State of β-1,3-Glucan and Hairdressing Power/Set-Keeping Power

Using β-1,3-glucan as a representative of heat-gelling polymers, the inventors studied the relationship between the gelling state in the cosmetic preparation and the hairdressing power/set-keeping power.

Namely, in the hairdressing cosmetic preparations, an aqueous dispersion of powder of curdlan in an ungelled state (Test Example 22), a dissolved neutralized gel state of curdlan gelled with the above-mentioned alkali (Test Example 23), a low-set gel of curdlan in a reversible heat-gelling state gelled at 60° C. (Test Example 24), and a high-set gel of curdlan in an irreversible heat-gelling state gelled at 90° C. (Test Example 25) were used as the polymers for the emulsified compositions of the above-mentioned Test Examples 11 to 21, and their hairdressing power and set-keeping power were determined. The hairdressing power was compared with that in the case using carboxy methyl cellulose (Test Example 26).

The dissolved neutralized gel of Test Example 23 was prepared by the following method.

(Preparation of 1% Curdlan Dissolved Neutralized Gel)

To 1 part by weight of curdlan, 98.18 parts by weight of purified water were added and, with 0.44 g of 10% aqueous sodium hydroxide solution being added thereto, the mixture was stirred, whereby a uniform solution was obtained. While thus obtained curdlan solution was stirred with a homogenizer, 0.38 g of 10% aqueous hydrochloric acid solution was added thereto. After being stirred at 7000 rpm for 1 minute, a uniform curdlan dissolved neutralized gel dispersion was obtained.

The results are shown in the following Table 5.

TABLE 5

| Test Example No. | Polymer | Hairdressing power | Set-keeping power |
|---|---|---|---|
| 22 | Powder dispersion | 1.8 | ⊚ |
| 23 | Dissolved neutralized gel | 1.8 | ⊚ |
| 24 | Low-set gel | 1.2 | ○ |
| 25 | High-set gel | 0.8 | ○ |
| 26 | Control (Carboxy methyl cellulose) | 1.8 | X |

As can be seen from Table 5, when a high-set gel in an irreversible heat-gelling state was used, the hairdressing power was inferior to that in the other gelling state, although the set-keeping power was not bad. Also, the hairdressing cosmetic preparations compounded with the powder dispersion in an ungelled state or in a dissolved neutralized gel considered to be in a gelling state different from the heat-gelling state exhibited particularly excellent effects.

Accordingly, it is presumed that the gelling state of polymers and the hairdressing power/set-keeping power are closely related to each other.

IV. Heating Condition after Application and Hairdressing Power/Set-Keeping Power Therefore, the inventors applied the above-mentioned emulsified compositions including the powder dispersion to hair as mentioned above, and then further studied their hairdressing power and set-keeping power with reference to their drying conditions.

The results are shown in Table 6.

TABLE 6

| Drying Condition | Hairdressing power | Set-keeping power |
|---|---|---|
| Hot wind at 85° C. | ⊚ | ⊚ |
| Hot wind at 50° C. | ○ | ○ |
| Wind at room temp. | Δ | ○ |

As can be seen from Table 6, although high hairdressing power and set-keeping power were obtained when dried with a hot wind at 85° C. at which powdery β-1,3-glucan in an ungelled state can shift to a high-set gel, the high hairdressing power and set-keeping power were insufficient when dried at a temperature thereunder.

From the foregoing results, it is presumed that β-1,3-glucan in a state other than the high-set gel state is dried by way of the high-set gel state on hair to enhance the hairdressing power and set-keeping power.

V. Existence of Water and Hairdressing Power/Set-Keeping Power

Hairdressing cosmetic preparations having the compositions of the following Table 7 were prepared, and the relationship between whether there was water upon heating and the hairdressing power/set-keeping power was studied according to their respective sensory evaluations.

TABLE 7

| Ingredients | Test Example 27 | Test Example 28 |
|---|---|---|
| Curdlan ungelled powder | 0.5 | 0.5 |
| Acrylic resin alkanol amine solution | 3.5 | 3.5 |
| Cetyl alcohol | 0.1 | 0.1 |
| Silicone oil | 0.3 | 0.3 |
| Purified water | 50.0 | — |
| Ethanol | Balance | Balance |

Each of the compositions of the above-mentioned Test Examples 27 and 28 was applied to hair sufficiently dried after washing and hair in such a wet state that droplets were lightly wiped off after washing, and then was dried with a hot wind at 85° C. Table 8 shows the hairdressing power and set-keeping power in this case.

TABLE 8

| Test Ex. No. | Condition | Hairdressing power | Set-keeping power |
|---|---|---|---|
| 27 | Dry | ⊚ | ⊚ |
|  | Wet | ⊚ | ⊚ |
| 28 | Dry | Δ | Δ |
|  | Wet | ⊚ | ⊚ |

From Table 8, it can be seen that desirable hairdressing power and set-keeping power are hard to obtain in Test Example 28 containing no purified water. even if it is applied to hair in a dried state and blown with a hot wind.

However, it has become clear that, when Test Example 27 containing water is applied or when Test Example 28 is applied to hair in a wet state, excellent hairdressing power and set-keeping power will be obtained by heating and drying arc carried out with a hot wind at 85° C. thereafter.

VI. Compounding Fine Particle Powder

Into Test Example 27, 0.3% by weight of each powder in Table 9 was added to prepare a hairdressing cosmetic preparation (the increase by powder being adjusted with ethanol). Thus obtained sample was applied to hair in a dry state of 20 female panels, and a blow was effected with a hot wind at 85° C. while the hair was straightened with a brush. The easiness in catching by the brush (easiness in blow), lightness, touch, and hairdressing power after finishing in this case were surveyed by questionnaires, and were evaluated according to the following standards:

⊚: 16 panels or more evaluated favorable

○: 10 to 15 panels evaluated favorable

Δ: 5 to 9 panels evaluated favorable

X: 4 or less panels evaluated favorable

TABLE 9

| Powder | Average particle size(μm) | Easiness in blow | Lightness | Touch | Hairdressing power |
|---|---|---|---|---|---|
| None (Test Ex. 27) | — | Δ | ⊚ | ⊚ | ⊚ |
| Fine particle TiO$_2$ | 0.01 | ⊚ | ⊚ | ⊚ | ⊚ |
| Titania sol*1 | 0.01 | ⊚ | ⊚ | ⊚ | ⊚ |
| Fine particle silica*2 | 0.05 | ⊚ | ⊚ | ⊚ | ⊚ |
| TiO$_2$ | 0.3 | ⊚ | ○ | Δ | ⊚ |
| Silica | 0.5 | ⊚ | ○ | Δ | ⊚ |
| Talc | 1.0 | ⊚ | ○ | Δ | ⊚ |
| Nylon powder | 1.0 | ⊚ | ○ | Δ | ⊚ |

*1: aqueous dispersion containing 30% of silica-surface-treated fine particle titanium dioxide (manufactured by Ishihara Sangyo Co., Ltd.)
*2: Aerosyl (manufactured by Nippon Aerosyl Co., Ltd.)

In the case containing no powder (Test Example 27), as can be seen from Table 9, hair was so light upon blowing that it was hard to catch hair by the brush, thus making the blow difficult.

In the case containing powder, by contrast, because there was an appropriate tension upon blowing, it was easy to catch hair by the brush, thereby making the blow easier. However, in the case of powders having a size in the pigment class, the lightness and touch after finishing would deteriorate, whereby it has become clear that fine particle powder is preferred as powder.

In the following, preferable Compounding Examples of the present invention will be shown.

Compounding Example 1

Hair Spray

| Curdlan | 0.10 wt % |
|---|---|
| t-Octyl acryl amide/acrylic acid/t-butylaminoethyl methacrylate copolymer | 5.00 |
| 2-Amino-2-methyl-1-propanol | 0.91 |
| Ethanol | 23.99 |
| Dimethyl ether | 60.00 |
| Plants extract | Q.S. |
| Water | Balance |

Compounding Example 2

Setting Lotion

| | |
|---|---|
| Curdlan | 0.25 wt % |
| Propylene glycol | 0.50 |
| Perfume oil | Q.S. |
| Methyl paraben | 0.10 |
| Propyl paraben | 0.10 |
| Plants extract | Q.S. |
| Water | Balance |

Compounding Example 3

Foamy Setting Preparation

| | |
|---|---|
| Curdlan | 0.2 wt % |
| Cetyl trimethyl ammonium chloride | 0.3 |
| Perfume oil | Q.S. |
| 1,2-Dibromo-2,4-dicyanobutane | 0.2 |
| Water | Balance |

This mixture and butane are filled into an aerosol container of aluminum with a ratio of 92:8.

Compounding Example 4

Gel Having Hairdressing Effect

| | |
|---|---|
| Curdlan | 0.2 wt % |
| Carboxy vinyl polymer | 0.3 |
| Perfume oil | Q.S. |
| Ethanol | 20.0 |
| Plants extract | Q.S. |
| Water | Balance |

Compounding Example 5

Color Hairdressing Preparation

| | |
|---|---|
| Curdlan | 0.1000 wt % |
| Vinyl pyrrolidone/vinyl acetate copolymer | 2.1000 |
| Perfume | Q.S. |
| 1-Amino-4-(2',3'-dihydroxypropyl)amino-5-chloro-2-nitrobenzene | 0.0700 |
| Basic Brown 17 (C.I. 12 251) | 0.0500 |
| Basic Blue 7 (C.I. 42 595) | 0.0100 |
| Basic Violet (C.I. 42 510) | 0.0023 |
| Ethanol | 50.0000 |
| Water | Balance |

Compounding Example 6

Liquid Setting Preparation

| | |
|---|---|
| Curdlan | 0.6 wt % |
| Vinyl pyrrolidone/dimethylaminoethyl methacrylate copolymer | 0.5 |
| Perfume | Q.S. |
| Ethanol | 16.0 |
| Water | Balance |

Compounding Example 7

Setting Lotion

| | |
|---|---|
| Curdlan | 0.30 wt % |
| Vinyl acetate/crotonic acid/vinyl neodecanoate copolymer | 1.50 |
| Betaine monohydrate | 0.50 |
| 1,2-Dibromo-2,4-dicyanobutane | 0.20 |
| Perfume | Q.S. |
| Water | Balance |

Compounding Example 8

Foamy Setting Preparation

| | |
|---|---|
| Curdlan | 0.2 wt % |
| t-Octyl acrylamide/acrylic acid/t-butyric acid/t-butylaminoethyl methacrylate copolymer | 1.0 |
| Decyl polyglucose | 0.2 |
| Polypropylene glycol(1)-polyethylene glycol(9)-lauryl glycol ether | 0.2 |
| 2-Amino-2-methyl-1-propanol | 0.2 |
| Perfume | Q.S. |
| Water | Balance |

This mixture and propellant gas consisting of propane/butane are filled into a container with a ratio of 9:1.

Compounding Example 9

Foamy Setting Preparation

| | |
|---|---|
| Curdlan | 0.50 wt % |
| Polyvinyl pyrrolidone | 0.75 |
| Vinyl pyrrolidone/vinyl acetate copolymer | 0.75 |
| Cetyl trimethyl ammonium chloride | 0.30 |
| Perfume | Q.S. |
| Water | Balance |

This mixture (90%) is filled into a container together with propellant gas such as propane/butane (8%) and dimethyl ether (2%).

Compounding Example 10

Pump Spray (55% VOC)

| | |
|---|---|
| Curdlan | 0.05 wt % |
| Polyacrylic acid | 1.68 |
| 2-Amino-2-methyl-1-propanol | 0.18 |
| Perfume | Q.S. |
| Ethanol | 55.00 |
| Water | Balance |

Compounding Example 11

Hair Spray

| | |
|---|---|
| Curdlan | 0.1 wt % |
| Vinyl acetate/vinyl propionate/crotonic acid copolymer | 7.5 |
| Perfume | Q.S. |
| Isopropanol | 45.0 |
| Water | Balance |

Compounding Example 12

Hair Gel

| | |
|---|---|
| Curdlan | 1.0 wt % |
| Carboxy Vinyl polymer | 0.7 |
| Polyvinyl pyrrolidone | 1.0 |
| Glycerin | 2.0 |
| Sodium hydroxide | Q.S. |
| Ethanol | 20.0 |
| Polyoxyethylene octyl dodecyl ether | 0.8 |
| Perfume | Q.S. |
| Chelating agent | Q.S. |
| Purified water | Balance |

Compounding Example 13

Water Grease

| | |
|---|---|
| Curdlan | 2.0 wt % |
| Carboxy vinyl polymer | 0.5 |
| Glycerin | 50.0 |
| Sodium hydroxide | Q.S. |
| Ethanol | 10.0 |
| Polyoxyethylene octyl dodecyl ether | 0.5 |
| Perfume | 0.1 |
| Chelating agent | 0.1 |
| Purified water | Balance |

Compounding Example 14

Hair Cream

| | |
|---|---|
| Curdlan | 0.4 wt % |
| Decamethylcyclopentasiloxane | 15.0 |
| Vaseline | 15.0 |
| Bleached bees wax | 2.0 |
| Methyl paraben | 0.1 |
| Carboxy vinyl polymer | 0.1 |
| Xanthan gam | 0.1 |
| Glycerin | 5.0 |
| Polyoxyethylene hydrogenated castor oil | 0.1 |
| Chelating agent | 0.1 |
| Coloring agent | Q.S. |
| Sodium hydroxide | Q.S. |
| Purified water | Balance |

Compounding Example 15

Treatment Lotion

| | |
|---|---|
| Curdlan | 0.7 wt % |
| 1,3-Butylene glycol | 2.0 |
| Glycerin | 1.0 |
| Stearyl trimethyl ammonium chloride | 0.5 |
| Highly polymerized methylpolysiloxane | 1.0 |
| Collagen hydrolysate | 1.0 |
| Perfume | Q.S. |
| Ultraviolet absorbent | Q.S. |
| Methyl paraben | Q.S. |
| Ethanol | 50.0 |
| Purified water | Balance |

Compounding Example 16

Foamy Setting Preparation

| | |
|---|---|
| Curdlan | 0.9 wt % |
| N-methacryloyl oxyethyl N,N-dimethyl ammonium-α-N-methyl carboxy betaine/alkyl methacrylate copolymer | 3.0 |
| Titanium oxide | 0.2 |
| Glycerin | 6.0 |
| Trioctanoin | 1.0 |
| Perfume oil | Q.S. |
| 1,2-Dibromo-2,4-dicyanobutane | 0.2 |
| Water | 88.0 |

This mixture and butane are filled into an aerosol container of aluminum with a ratio of 92:8.

Compounding Example 17

Gel Having Hairdressing Effect

| | |
|---|---|
| Curdlan | 0.5 wt % |
| Carboxy vinyl polymer | 0.5 |
| Vinyl acetate/vinyl pyrrolidone copolymer | 5.0 |
| Perfume oil | 0.15 |
| Ethanol | 20.0 |
| Water | 73.4 |
| Plants extract | Q.S. |

Compounding Example 18

Liquid Setting Preparation

| | |
|---|---|
| Curdlan | 0.8 wt % |
| Vinyl pyrrolidone/dimethyl amino ethyl methacrylate cationized copolymer | 5.0 |
| Zinc oxide | 0.3 |
| Perfume | Q.S. |
| Water | 93.0 |

Compounding Example 19

Hair Gel

| | |
|---|---|
| Curdlan | 0.2 wt % |
| Carboxy vinyl polymer | 0.8 |
| Acrylic resin alkanol amine | 0.3 |
| Glycerin | 5.0 |
| Sodium hydroxide | Q.S. |
| Ethanol | 20.0 |
| Polyoxyethylene octyl dodecyl ether | 0.8 |
| Perfume | 0.1 |
| Chelating agent | 0.3 |
| Purified water | 74.5 |

Compounding Example 20

Hair Spray

| | |
|---|---|
| Curdlan | 0.2 wt % |
| N-methacryloyl oxyethyl N,N-dimethyl ammonium-α-N-methyl carboxy betaine/alkyl methacrylate copolymer | 3.0 |
| 2-Amino-2-methyl-1-propanol | 0.9 |
| Trioctanoin | 2.0 |
| Water | 13.0 |
| Ethanol | 25.0 |
| Dimethyl ether | 55.0 |
| Plants extract | Q.S. |

Compounding Example 21

Setting Lotion

| | |
|---|---|
| Curdlan | 0.7 wt % |
| Butylene glycol | 2.5 |
| Dimethicon | 1.0 |
| Carrageenan | 0.3 |
| Titanium oxide | 0.2 |
| Methyl paraben | 0.2 |
| Water | 94.0 |
| Plants extract | Q.S. |

What is claimed is:

1. A hairdressing cosmetic preparation comprising a heat-gelling polymer in a hairdressing cosmetic;
   wherein said heat-gelling polymer is curdlan, which is produced by Alcaligenes faecalis var. myxogens or various strains of Agrobacterium or Rhizobium;
   wherein said curdlan becomes a gel upon heating at 60° C. or higher;
   wherein said hairdressing cosmetic is one selected from the group consisting of hair cream, hair lotion, hair foam, hair gel, hair mist, hair spray, hair liquid, and hair wax; and
   wherein said hairdressing cosmetic shapes and fixes hair which is accomplished by application said heat-gelling polymer to said hair and fixing said hair with a hot wind at a temperature of 60° C. or higher.

2. A hairdressing cosmetic preparation comprising a heat-gelling polymer in a hairdressing cosmetic;
   wherein said heat-gelling polymer becomes a gel upon heating at 60° C. or higher;
   wherein said heat-gelling polymer is β-1,3-xylan;
   wherein said hairdressing cosmetic is one selected from the group consisting of hair cream, hair lotion, hair foam hair gel hair mist, hair spray, hair liquid, and hair wax; and wherein said hairdressing cosmetic shapes and fixes hair.

3. The hairdressing cosmetic preparation according to claim 1, wherein said heat-gelling polymer is dispersed into the hairdressing cosmetic preparation; and wherein said heat-gelling polymer is an ungelled powder or a dissolved neutralized gel.

4. The hairdressing cosmetic preparation according to claim 1, further comprising water.

5. The hairdressing cosmetic preparation according to claim 1, wherein the heat-gelling polymer is 0.001% to 10% by weight of the hairdressing cosmetic preparation.

6. The hairdressing cosmetic preparation according to claim 1, further comprising a fine particle powder.

7. The hairdressing cosmetic preparation according to claim 6, wherein the fine particle powder is a fine particle of titanium dioxide.

8. The hairdressing cosmetic preparation according to claim 6, wherein the fine particle powder is a fine particle of silica.

9. The hairdressing cosmetic preparation according to claim 6, wherein the fine particle powder is a silica-surface-treated fine particle of titanium dioxide.

10. A hairdressing method comprising the steps of
    shaping hair by applying thereto a composition comprising a heat-gelling polymer, wherein said composition comprises curdlan; and
    fixing the hair with a hot wind, wherein said hot wind is at a temperature of 60° C. or higher.

11. The hairdressing method according to claim 10, wherein said composition contains water or said hair is in a wet state.

12. A hairdressing cosmetic preparation comprising a heat-gelling polymer in a hairdressing cosmetic;
    wherein said heat-gelling polymer becomes a gel upon heating at 60° C. or higher;
    wherein said heat-gelling polymer is a heat-coagulable protein or collagen;
    wherein said hairdressing cosmetic is one selected from the group consisting of hair cream, hair lotion, hair foam, hair gel, hair mist, hair spray, hair liquids and hair wax;
    and wherein said hairdressing cosmetic shapes and fixes hair.

13. A hairdressing cosmetic preparation comprising a heat-gelling polymer in a hairdressing cosmetic;
    wherein said heat-gelling polymer becomes a gel upon heating at 60° C. or higher;
    wherein said heat-gelling polymer is at least one selected from the group consisting of scleroglucan, sclerotan, schizophyllan, lentinan, paramylon, callose, and laminaran;
    wherein said hairdressing cosmetic is one selected from the group consisting of hair cream hair lotion, hair foam, hair gel hair mist, hair spray hair liquid, and hair wax; and wherein said hairdressing cosmetic shapes and fixes.

14. A hairdressing cosmetic preparation according to claim 1, wherein said heat-gelling polymer becomes a thermally reversible gel by cooling after heating at about 60° C.

15. A hairdressing cosmetic preparation according to claim 1, wherein said heat-gelling polymer becomes a thermally irreversible gel by heating at 80° C. or higher.

16. A hairdressing cosmetic preparation according to claim 1, wherein said dissolved neutralized gel is a curdlan which is dissolved in an alkaline solution and then neutralized by at least one selected from the group consisting of an acid, carbonic acid gas, dialysis membrane, and a cation.

17. The hairdressing method according to claim 10, wherein said hot wind is 80° C. or higher.

18. A method for shaping and fixing hair comprising applying the hairdressing cosmetic preparation according to claim 1 to hair of a person.

* * * * *